United States Patent
Farer et al.

(10) Patent No.: US 6,315,990 B1
(45) Date of Patent: *Nov. 13, 2001

(54) COSMETIC COMPOSITION HAVING FLUOROSILANE COATED PARTICULATES

(75) Inventors: Alan Farer, Kinnelon, NJ (US); Shari R. Martin, Suffern, NY (US)

(73) Assignee: Avon Products, Inc., New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/467,442

(22) Filed: Dec. 20, 1999

(51) Int. Cl.$^7$ .................................. A61K 7/025
(52) U.S. Cl. .................. 424/64; 424/401; 424/63; 424/69; 424/70.7; 428/405
(58) Field of Search ................. 424/401, 63, 64, 424/69, 70.7; 428/405

(56) References Cited

U.S. PATENT DOCUMENTS 5,458,976 * 10/1995 Horino et al. .................. 428/405
5,482,547   1/1996 Bugnon et al. .................. 106/493

FOREIGN PATENT DOCUMENTS

401160907A * 6/1989 (JP).
402202941A * 8/1990 (JP).
   7053326   2/1995 (JP).
408208418A * 8/1996 (JP).

* cited by examiner

Primary Examiner—Thurman K. Page
Assistant Examiner—Liliana Di Nola-Baron
(74) Attorney, Agent, or Firm—Ohlandt, Greeley, Ruggiero & Perle, LLP

(57) ABSTRACT

A cosmetic composition having particulates coated with fluorosilane, such as a pigment and/or filler coated with fluorosilane is provided. The cosmetic composition can be a blush, a concealer, an eye shadow, a lipstick, a liquid make-up, a mascara, a moisturizer, or a powder. The present invention also provides methods of (a) reducing staining potential of a lipstick on a person, (b) improving water and/or oil resistance in cosmetic compositions, especially in a mascara, (c) reducing oil breakthrough in a facial product, and (d) reducing color drift in a powder cosmetic during wear.

13 Claims, No Drawings

COSMETIC COMPOSITION HAVING FLUOROSILANE COATED PARTICULATES

BACKGROUND OF THE INVENTION

1. Field of the Invention

The present invention relates to cosmetic compositions. More particularly, the present invention relates to cosmetic compositions having fluorosilane-coated particulates. The cosmetic composition may be a blush, a concealer, an eye shadow, a lipstick, a lip liner, an eye liner, a liquid or cream compact make-up, a mascara, a moisturizer, a face powder or pressed powder. It is believed that the particulates coated with fluorosilane according to the present invention can be incorporated into any composition intended for any cosmetic use.

The present invention further relates to methods of reducing (a) color drift in a pigmented cosmetic, especially a pigmented face powder or blush cosmetic during wear; (b) staining potential of a lipstick on a person; and (c) oil breakthrough in facial products. The present invention also relates to methods of improving or increasing (a) comfort of cosmetic products; and (b) water resistance in cosmetic products, especially in a mascara. cosmetic products; and (b) water resistance in cosmetic products, especially in a mascara.

2. Description of the Prior Art

U.S. Pat. No. 5,482,547 to Bugnon et al. is directed to a paint or varnish containing an organic pigment coated with a silicate.

Japan Patent No. 7053326 is directed to a makeup cosmetic material that contains modified powder prepared by coating powder with methylhydrogensiloxane and heat-treating and blending modified powder coated with a fluorine containing compound.

Fluorosilanes have been used in construction and for coating glass. However, heretofore, tridecafluorooctyltriethoxy silane-coated cosmetic pigments are not known.

Some cosmetic products, particularly cosmetic products having colored compositions, suffer from stability problems that lead to an aesthetically unattractive appearance. These problems include settling, migration and floatation of colorants in nail enamel, color drift in a face powder or blush cosmetic during wear, oil breakthrough in facial products, and staining of a lipstick on a person.

Despite the continuous efforts of the cosmetic industry to develop cosmetic compositions that are more stable and aesthetically pleasing under normal use conditions, the appearance of a cosmetic after application deteriorates rapidly leading to an aesthetically unattractive appearance of the wearer of the cosmetic.

To overcome the instability problem of certain cosmetics and to minimize or eliminate the aesthetic deterioration of certain cosmetics during normal use, the present invention provides cosmetic compositions that employ particulates, such as pigments, that are coated with fluorosilane.

The compositions of the present invention are stable for an extended period of time, and have enhanced wear resistance due to the oil and water resistant nature of the fluorosilane coated cosmetic particulates. Thus, since the compositions of the present invention will not be affected by moisture or oil from the skin, they will not intensify the color of the product (known as "blooming" of the product). Accordingly, truer color of the product is maintained.

SUMMARY OF THE INVENTION

It is an object of the present invention to provide cosmetic compositions having particulates, at least some of which, and preferably most of which, are coated with fluorosilane.

It is another object of the present invention to provide such cosmetic compositions that can be a blush, a concealer, an eye shadow, a lipstick, a liquid or cream compact make-up, a mascara, a moisturizer, or a powder, such as a face powder or a pressed powder.

It is still another object of the present invention to provide a method of reducing color drift in cosmetic compositions, such as a liquid or cream compact make-up or a face or blush powder, during wear.

It is a further object of the present invention to provide a method of reducing staining potential of a lipstick on a person.

It is still a further object of the present invention to provide a method of improving or increasing water resistance in cosmetic compositions, especially a mascara.

DETAILED DESCRIPTION OF THE INVENTION

The present invention provides cosmetic compositions having particulates or particulate material coated with fluorosilane.

The term "fluorosilane" in the present invention refers to a silicon-containing compound having a hydrocarbyl group substituted by at least one fluorine atom and a reactive hydrocarbyloxy group capable of displacement by a nucleophile.

The term "hydrocarbyl" in the present invention refers to a linear, branched and cyclic group containing carbon and hydrogen such as an alkane, an alkene, an alkyne and an aryl group. The hydrocarbyl group may be additionally interrupted and/or substituted by one or more of the following: a halogen, a cyano, a keto, an ester, hydroxyl, carboxyl, oxygen, sulfur, or nitrogen.

The term "perfluoro hydrocarbyl" in the present invention refers to a fully fluorinated hydrocarbyl group.

The fluorosilane is represented by the formula:

$$R_f Si (OR)_3$$

wherein $R_f$ is a $C_4$–$C_{16}$ hydrocarbyl group having at least one fluorine atom, and wherein R is a $C_1$–$C_6$ hydrocarbyl group.

The preferred fluorosilane is represented by the formula:

$$R_f' CH_2CH_2Si (OR)_3$$

wherein $R_f'$ is a $C_4$–$C_{14}$ perfluoro hydrocarbyl group, and wherein R is methyl or ethyl.

An example of the preferred fluorosilane is tridecafluorooctyltriethoxy silane represented by the formula:

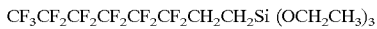

$$CF_3CF_2CF_2CF_2CF_2CF_2CH_2CH_2Si (OCH_2CH_3)_3$$

Tridecafluorooctyltriethoxy silane is available from Sivento, Piscataway, N.J., under the trade name DYNASILANE® F 8261.

The particulates coated with fluorosilane according to the present invention can be organic pigments, inorganic pigments, organic fillers, inorganic fillers, or any combination thereof.

Examples of the organic particulate pigments include azo, xanthene, quinone, lakes, especially aluminum lakes, strontium lakes, barium lakes, FD&C and D&C Red 6, Red 7, Red 30, Red 34, Yellow 5, Blue 1, or derivatives thereof, or mixtures thereof. Examples of the inorganic particulate pigments are iron oxide, especially red, yellow and black iron oxides, titanium dioxide, zinc oxide, potassium ferricyanide ($K_3Fe(CN)_6$), potassium ferrocyanide ($K_4Fe(CN)_6$), potassium ferrocyanide trihydrate ($K_4Fe(CN)_6 \cdot 3H_2O$), and mixtures thereof. Examples of the organic fillers include starch. Examples of the inorganic fillers include talc, mica, silica, and mixtures thereof.

A preferred tridecafluorooctyltriethoxy silane-coated pigment includes tridecafluorooctyltriethoxy silane-coated black ore iron oxide, and tridecafluorooctyltriethoxy silane-coated red iron oxide. Tridecafluorooctyltriethoxy silane-coated red iron oxide ($Fe_2O_3$) is available from Cardre Pigment Technologies, Inc., South Plainfield, N.J.

The amount of fluorosilane is about 0.01 percentage by weight (wt %) to about 5 wt %, and the amount of particulates is about 95 wt % to about 99.99 wt %, of the total weight of the fluorosilane coated particulate. Preferably, the amount of fluorosilane is about 2 wt %, and the amount of particulates is about 98 wt % of the total weight of the fluorosilane coated particulate.

The particulates coated with fluorosilane are about 0.1 wt % to about 40 wt % of the total weight of the composition. Preferably, the particulate coated with fluorosilane is about 1 wt % to about 25 wt % of the total weight of the composition.

While, in general, the fluorosilane is about 0.0005 wt % to about 1.5 wt % of the total weight of the cosmetic composition, the amount of fluorosilane varies within the range depending upon its intended product. For example, the fluorosilane is about 0.01 wt % to about 1.5 wt % of the total weight in a pressed face powder or blush. The fluorosilane is about 0.01 wt % to about 0.5 wt % of the total weight in a mascara. The fluorosilane is about 0.0015 wt % to about 0.30 wt % of the total weight of the composition in a lip product. It is about 0.01 wt % to about 0.5 wt % of the total weight in a liquid make-up. The fluorosilane is about 0.01 wt % to about 1.5 wt % of the total weight of the composition in an eye shadow.

A cosmetic composition of the present invention can be an unpigmented cosmetic composition having fluorosilane coated particulates. Such unpigmented compositions include, for example, a skin treatment product, and a sunscreen. In such cases, the fluorosilane is about 0.01 wt % to about 0.50 wt % of the total weight of the unpigmented composition.

In general, fluorine-treated particulates do not dissolve or disperse in water, hydrocarbon solvents or common organic solvents. Fluorosilanes are also insoluble in water and have limited solubility in hydrocarbon and other common organic solvents, but can be dispersed in ethanol. It has been surprisingly found that fluorosilane-containing water-based compositions can be easily prepared according to the present invention. For example, the lipsticks of the present invention can be prepared by dispersing particulate material coated with fluorosilane, such as pigments and/or fillers coated with fluorosilane, into a slurry. Thereafter, the slurry is added to a lipstick formulation.

Ordinarily, when organic pigments, such as common organic colorants, are used in a lipstick formulation, the organic pigment interacts with the moisture on the lips. Such interaction causes staining and dries the lips. According to the present invention, coating organic pigments with fluorosilane in a lipstick formulation produces a lipstick with reduced staining potential and improved moisturization. Specifically, the water repellent nature of the fluorosilane coating prevents and protects the pigments from interacting with moisture. Thus, the lipstick of the present invention minimizes the staining of the lips and results in a greater amount of moisture being bound to the lips. In addition to water proofing properties, the lipstick of the present invention also has improved wear, moisturization, and reduced color drift.

A blush or face powder of the present invention can be prepared by coating pigment and/or filler particulates with fluorosilane in such powders and thereafter mixing together these ingredients to obtain a uniform composition. The resulting blush or face powder has enhanced wear resistance. Such powders during wear display enhanced water proofing and reduced color drift, which is otherwise caused by the blooming of shade during the day due to its interaction with skin lipids and with skin moisture vapor. In addition to the coated pigments, the blush or face powder formulations will preferably have filler particulates as well coated with fluorosilane.

In a blush or a face powder composition, the amount of pigments coated with fluorosilane are about 1 wt % to about 15 wt % of the total weight of the composition. As stated before, the amount of fluorosilane is about 0.01 wt % to about 1.5 wt %.

A moisturizer of the present invention can be prepared by dispersing particulates, such as pigments and/or fillers, coated with fluorosilane into a slurry and thereafter adding the slurry to a moisturizer formulation. The coated particulates of the present invention when added to the moisturizer vehicle causes the formation of an oil and water repellent film, which produces a moisturizer that displays reduced oil breakthrough. The most commonly used particulates in this case are talc, mica, silica, iron oxides and titanium dioxide. To achieve these benefits, about 3 wt % to about 20 wt %, based on the total weight of the composition, of the fluorosilane-coated particulates are in the moisturizer composition, with the fluorosilane being about 0.05 wt % to about 0.5 wt %.

Thus, fluorosilane coated particulates, such as pigments, fillers or a combination of pigments and fillers, of the present invention in a cosmetic composition improve wear resistance and water proofing properties of blush, powder and lip cosmetics. In a face powder, it improves the color drift over time.

In addition to the coated particulates, the cosmetic compositions can also include one or more of the following: a chelating agent, an emollient, an emulsifier, a film former, a fragrance, a humectant, a plasticizer, a preservative, a resin, a retinoid, a skin penetration enhancer, a solvent, a stabilizer, a sunscreen, a surfactant, a thickener, a vitamin and a wax.

The present invention has been described with particular reference to the preferred embodiments thereof. It will be obvious that variations and modifications may be made therein without departing from the spirit and scope of the present invention as defined by the following claims. Also, singular used in the application can also mean plural of the same ingredient unless otherwise indicated. Also, improving means increasing unless otherwise indicated.

Wherefore we claim:

1. A cosmetic composition for application to skin, lips or eyelashes comprising:
    a plurality of particulates, at least some of which are coated with fluorosilane;
    a vehicle suitable for application to the skin, lips or eyelashes; and
    an ingredient selected from the group consisting of: a chelating agent, a film former, a plasticizer, a resin, a retinoid, a skin penetration enhancer, a stabilizer, a sunscreen, a vitamin, a wax, and any combinations thereof;
    wherein the composition is a product selected from the group consisting of:

a powder or a blush, wherein said fluorosilane is about 0.01 wt % to about 1.5 wt % of the total weight of the cosmetic composition;

an eye shadow, wherein said fluorosilane is about 0.01 wt % to about 1.5 wt % of the total weight of the cosmetic composition;

a lip product, wherein said fluorosilane is about 0.0015 wt % to about 0.30 wt % of the total weight of the cosmetic composition;

a liquid make-up, and wherein said fluorosilane is about 0.01 wt % to about 0.5 wt % of the total weight of the cosmetic composition;

a mascara, wherein said fluorosilane is about 0.01 wt % to about 0.5 wt % of the total weight of the cosmetic composition;

a concealer;

a cream make-up; and a moisturizer.

2. The cosmetic composition according to claim 1, wherein said fluorosilane is represented by the formula:

$$R_f Si(OR)_3$$

wherein $R_f$ is a $C_4$–$C_{16}$ hydrocarbyl having at least one fluorine atom and R is a $C_1$–$C_6$ hydrocarbyl.

3. The cosmetic composition according to claim 2, wherein said fluorosilane is represented by the formula:

$$R_f'CH_2CH_2Si(OR)_3$$

wherein $R_f'$ is a $C_4$–$C_{14}$ perfluoro hydrocarbyl and R is methyl or ethyl.

4. The cosmetic composition according to claim 3, wherein said fluorosilane is represented by the formula:

$$CF_3CF_2CF_2CF_2CF_2CF_2CH_2CH_2Si(OCH_2CH_3)_3.$$

5. The cosmetic composition according to claim 1, wherein said particulates are selected from the group consisting of pigments, fillers, and mixtures thereof.

6. The cosmetic composition according to claim 5, wherein said pigment is selected from the group consisting of organic pigments, inorganic pigments, and a combination thereof.

7. The cosmetic composition according to claim 5, wherein said pigment is an inorganic pigment selected from the group consisting of an iron oxide, titanium dioxide, zinc oxide, potassium ferricyanide ($K_3Fe(CN)_6$), potassium ferrocyanide ($K_4Fe(CN)_6$), potassium ferrocyanide trihydrate ($K_4Fe(CN)_6.3H_2O$), and mixtures thereof, and wherein said filler is selected from the group consisting of mica, talc, silica, starch, and mixtures thereof.

8. A method of reducing staining potential of a lip product on a person, comprising applying to the person a lip product comprising:

a plurality of particulates, at least some of which are coated with fluorosilane;

a vehicle suitable for application to the lips; and an ingredient selected from the group consisting of: a chelating agent, a film former, a plasticizer, a resin, a retinoid, a skin penetration enhancer, a stabilizer, a sunscreen, a vitamin, a wax, and any combinations thereof;

wherein said fluorosilane is about 0.0015 wt % to about 0.30 wt % of the total weight of the lip product.

9. A method of improving water and/or oil resistance in a mascara on a person, comprising applying to a person a mascara comprising:

a plurality of particulates, at least some of which are coated with fluorosilane;

a vehicle suitable for application to the eyelashes; and an ingredient selected from the group consisting of: a chelating agent, a film former, a plasticizer, a resin, a retinoid, a skin penetration enhancer, a stabilizer, a sunscreen, a vitamin, a wax, and any combinations thereof;

wherein said fluorosilane is about 0.01 wt % to about 0.5 wt % of the total weight of the mascara.

10. A method of improving wear resistance of a cosmetic having a plurality of particulates comprising applying to a person a cosmetic composition comprising:

a plurality of particulates, at least some of which are coated with fluorosilane;

a vehicle suitable for application to the skin; and an ingredient selected from the group consisting of: a chelating agent, a film former, a plasticizer, a resin, a retinoid, a skin penetration enhancer, a stabilizer, a sunscreen, a vitamin, a wax, and any combinations thereof;

wherein said cosmetic composition is a product selected from the group consisting of a an eye shadow, and wherein said fluorosilane is about 0.01 wt % to about 1.5 wt % of the total weight of the cosmetic composition;

a liquid make-up, and wherein said fluorosilane is about 0.01 wt % to about 0.5 wt % of the total weight of the cosmetic composition;

a concealer; and a cream make-up.

11. A method of reducing oil breakthrough in a facial product on a person, comprising applying to the person a facial product comprising:

a plurality of particulates, at least some of which are coated with fluorosilane;

a vehicle suitable for application to the face; and an ingredient selected from the group consisting of: a chelating agent, a film former, a plasticizer, a resin, a retinoid, a, skin penetration enhancer, a stabilizer, a sunscreen, a vitamin, a wax, and any combinations thereof.

12. A method of reducing color drift in a powder cosmetic during wear on a person, comprising applying to the person a powder cosmetic comprising:

a plurality of particulates, at least some of which are coated with fluorosilane;

a vehicle suitable for application to skin; and an ingredient selected from the group consisting of: a chelating agent, a film former, a plasticizer, a resin, a retinoid, a skin penetration enhancer, a stabilizer, a sunscreen, a vitamin, a wax, and any combinations thereof;

wherein said powder cosmetic is a powder, a blush or an eye shadow, and wherein said fluorosilane is about 0.01 wt % to about 1.5 wt % of the total weight of the powder cosmetic.

13. The cosmetic composition according to claim 1, wherein the particulates are selected from the group consisting of organic fillers, inorganic fillers and mixtures thereof.

* * * * *

(12) EX PARTE REEXAMINATION CERTIFICATE (9876th)
United States Patent
Farer et al.

(10) Number: US 6,315,990 C1
(45) Certificate Issued: Oct. 16, 2013

(54) COSMETIC COMPOSITION HAVING FLUOROSILANE COATED PARTICULATES

(75) Inventors: Alan Farer, Kinnelon, NJ (US); Shari R. Martin, Suffern, NY (US)

(73) Assignee: PNC Bank, National Association, Pittsburgh, PA (US)

Reexamination Request:
No. 90/012,434, Aug. 15, 2012

Reexamination Certificate for:
Patent No.: 6,315,990
Issued: Nov. 13, 2001
Appl. No.: 09/467,442
Filed: Dec. 20, 1999

(51) Int. Cl.
*A61K 8/70* (2006.01)
*A61K 8/58* (2006.01)
*A61K 8/30* (2006.01)
*A61K 8/25* (2006.01)
*A61K 8/19* (2006.01)
*A61K 8/22* (2006.01)
*A61K 8/26* (2006.01)
*A61Q 1/10* (2006.01)
*A61Q 1/08* (2006.01)
*A61Q 1/02* (2006.01)
*A61Q 19/00* (2006.01)
*A61Q 1/12* (2006.01)
*A61Q 1/04* (2006.01)
*C09C 1/30* (2006.01)
*C09C 1/22* (2006.01)
*C09C 1/28* (2006.01)
*C09C 3/12* (2006.01)
*C09C 1/04* (2006.01)
*C09C 1/36* (2006.01)
*C09C 1/24* (2006.01)

(52) U.S. Cl.
USPC ............... 424/64; 424/401; 424/63; 424/69; 424/70.7; 428/405

(58) Field of Classification Search
None
See application file for complete search history.

(56) References Cited

To view the complete listing of prior art documents cited during the proceeding for Reexamination Control Number 90/012,434, please refer to the USPTO's public Patent Application Information Retrieval (PAIR) system under the Display References tab.

*Primary Examiner* — Dwayne Jones

(57) ABSTRACT

A cosmetic composition having particulates coated with fluorosilane, such as a pigment and/or filler coated with fluorosilane is provided. The cosmetic composition can be a blush, a concealer, an eye shadow, a lipstick, a liquid make-up, a mascara, a moisturizer, or a powder. The present invention also provides methods of (a) reducing staining potential of a lipstick on a person, (b) improving water and/or oil resistance in cosmetic compositions, especially in a mascara, (c) reducing oil breakthrough in a facial product, and (d) reducing color drift in a powder cosmetic during wear.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 2-4 and 13 are cancelled.

Claims 1 and 5-12 are determined to be patentable as amended.

New claims 14-24 are added and determined to be patentable.

1. A *water and oil repellant* cosmetic composition for application to skin, lips or eyelashes comprising:
    a plurality of particulates[, at least some of which are coated with] *selected from inorganic pigments, inorganic fillers, and lakes, said particulates having a coating consisting essentially of a* fluorosilane *having the formula* $CF_3CF_2CF_2CF_2CF_2CF_2CH_2CH_2Si(OCH_2CH_3)_3$;
    a vehicle suitable for application to the skin, lips or eyelashes; and
    an ingredient selected from the group consisting of: a chelating agent, a film former, a plasticizer, a resin, a retinoid, a skin penetration enhancer, a stabilizer, a sunscreen, a vitamin, a wax, and any combinations thereof;
    wherein the composition is a product selected from the group consisting of:
    a powder or a blush, wherein said fluorosilane is about 0.01 wt % to [about] 1.5 wt % of the total weight of the cosmetic composition;
    an eye shadow, wherein said fluorosilane is about 0.01 wt % to about 1.5 wt % of the total weight of the cosmetic composition;
    a lip product, wherein said fluorosilane is about 0.0015 wt % to about 0.30 wt % of the total weight of the cosmetic composition;
    a liquid make-up, and wherein said fluorosilane is about 0.01 wt % to about 0.5 wt % of the total weight of the cosmetic composition;
    a mascara, wherein said fluorosilane is about 0.01 wt % to about 0.5 wt % of the total weight of the cosmetic composition;
    a concealer;
    a cream make-up; and
    a moisturizer.

5. The cosmetic composition according to claim 1, wherein said particulates are selected from the group consisting of *inorganic* pigments, *inorganic* fillers, and mixtures thereof.

6. The cosmetic composition according to claim 5, wherein said pigment is [selected from the group consisting of organic pigments,] *an* inorganic [pigments, and a combination thereof] *pigment*.

7. The cosmetic composition according to [claim 5] *claim 6*, wherein said [pigment is an] inorganic pigment *is* selected from the group consisting of an iron oxide, titanium dioxide, zinc oxide, potassium ferricyanide ($K_3Fe(CN)_6$), potassium ferrocyanide ($K_4Fe(CN)_6$), potassium ferrocyanide trihydrate ($K_4Fe(CN)_6, 3H_2O$), and mixtures thereof, and wherein said *inorganic* filler is selected from the group consisting of mica, talc, silica, [starch,] and mixtures thereof.

8. A method of reducing staining potential of a lip product on a person, comprising applying to the person a *water and oil repellant* lip product comprising:
    a plurality of particulates[, at least some of which are coated with] *selected from inorganic pigments, inorganic fillers, and lakes, said particulates having a coating consisting essentially of a* fluorosilane *having the formula* $CF_3CF_2CF_2CF_2CF_2CF_2CH_2CH_2Si(OCH_2CH_3)_3$;
    a vehicle suitable for application to the lips; and
    an ingredient selected from the group consisting of: a chelating agent, a film former, a plasticizer, a resin, a retinoid, a skin penetration enhancer, a stabilizer, a sunscreen, a vitamin, a wax, and any combinations thereof;
    wherein said fluorosilane is about 0.0015 wt % to about 0.30 wt % of the total weight of the lip product.

9. A method of improving water and/or oil resistance in a mascara on a person, comprising applying to a person a *water and oil repellant* mascara comprising:
    a plurality of particulates[, at least some of which are coated with] *selected from inorganic pigments, inorganic fillers, and lakes, said particulates having a coating consisting essentially of a* fluorosilane *having the formula* $CF_3CF_2CF_2CF_2CF_2CF_2CH_2CH_2Si(OCH_2CH_3)_3$;
    a vehicle suitable for application to the eyelashes; and
    an ingredient selected from the group consisting of: a chelating agent, a film former, a plasticizer, a resin, a retinoid, a skin penetration enhancer, a stabilizer, a sunscreen, a vitamin, a wax, and any combinations thereof;
    wherein said fluorosilane is about 0.01 wt % to about 0.5 wt % of the total weight of the mascara.

10. A method of improving wear resistance of a cosmetic having a plurality of particulates comprising applying to a person a *water and oil repellant* cosmetic composition comprising:
    a plurality of particulates[, at least some of which are coated with] *selected from inorganic pigments, inorganic fillers, and lakes, said particulates having a coating consisting essentially of* fluorosilane *having the formula* $CF_3CF_2CF_2CF_2CF_2CF_2CH_2CH_2Si(OCH_2CH_3)_3$;
    a vehicle suitable for application to the skin; and
    an ingredient selected from the group consisting of: a chelating agent, a film former, a plasticizer, a resin, a retinoid, a skin penetration enhancer, a stabilizer, a sunscreen, a vitamin, a wax, and any combinations thereof;
    wherein said cosmetic composition is a product selected from the group consisting of a an eye shadow, and wherein said fluorosilane is about 0.01 wt % to about 1.5 wt % of the total weight of the cosmetic composition;
    a liquid make-up, and wherein said fluorosilane is about 0.01 wt % to about 0.5 wt % of the total weight of the cosmetic composition;
    a concealer; and
    a cream make-up.

11. A method of reducing oil breakthrough in a facial product on a person, comprising applying to the person a *water and oil repellant* facial product comprising:
    a plurality of particulates[, at least some of which are coated with] *selected from inorganic pigments, inorganic fillers, and lakes, said particulates having a coat-* ing consisting essentially of a fluorosilane having the formula $CF_3CF_2CF_2CF_2CF_2CF_2CH_2CH_2Si(OCH_2CH_3)_3$;

a vehicle suitable for application to the face; and an ingredient selected from the group consisting of: a chelating agent, a film former, a plasticizer, a resin, a retinoid, a, skin penetration enhancer, a stabilizer, a sunscreen, a vitamin, a wax, and any combinations thereof.

12. A method of reducing color drift in a powder cosmetic during wear on a person, comprising applying to the person a *water and oil repellant* powder cosmetic comprising:

a plurality of particulates[, at least some of which are coated with] selected from inorganic pigments, inorganic fillers, and lakes, said particulates having a coating consisting essentially of a fluorosilane having the formula $CF_3CF_2CF_2CF_2CF_2CF_2CH_2CH_2Si(OCH_2CH_3)_3$;

a vehicle suitable for application to skin; and an ingredient selected from the group consisting of: a chelating agent, a film former, a plasticizer, a resin, a retinoid, a skin penetration enhancer, a stabilizer, a sunscreen, a vitamin, a wax, and any combinations thereof;

wherein said powder cosmetic is a powder, a blush or an eye shadow, and wherein said fluorosilane is about 0.01 wt % to [about] 1.5 wt % of the total weight of the powder cosmetic.

14. The cosmetic composition according to claim 1, *wherein said fluorosilane comprises about 0.01 wt % to about 2.0 wt % of the total weight of the coated particulates.*

*15. A water and oil repellant cosmetic composition for application to skin, lips or eyelashes comprising:*

*a plurality of particulates selected from inorganic pigments, inorganic fillers, and lakes, said particulates having a coating consisting of a fluorosilane having the formula $CF_3CF_2CF_2CF_2CF_2CF_2CH_2CH_2Si(OCH_2CH_3)_3$;*

*a vehicle suitable for application to the skin, lips or eyelashes; and*

*an ingredient selected from the group consisting of: a chelating agent, a film former, a plasticizer, a resin, a retinoid, a skin penetration enhancer, a stabilizer, a sunscreen, a vitamin, a wax, and any combinations thereof;*

*wherein the composition is a product selected from the group consisting of:*

*a powder or a blush, wherein said fluorosilane is about 0.01 wt % to 1.5 wt % of the total weight of the cosmetic composition;*

*an eye shadow, wherein said fluorosilane is about 0.1 wt % about 1.5 % of the total weight of the cosmetic composition;*

*a lip product, wherein said fluorosilane is about 0.0015 wt % to about 0.30 wt % of the total weight of the cosmetic composition;*

*a liquid make-up, and wherein said fluorosilane is about 0.01 wt % to about 0.5 wt % of the total weight of the cosmetic composition;*

*a mascara, wherein said fluorosilane is about 0.01 wt % to about 0.5 wt % of the total weight of the cosmetic composition;*

*a concealer;*

*a cream make-up; and*

*a moisturizer.*

*16. The cosmetic composition according to claim 15, wherein said particulates are selected from the group consisting of inorganic pigments, inorganic fillers, and mixtures thereof.*

*17. The cosmetic composition according to claim 16, wherein said pigment is an inorganic pigment.*

*18. The cosmetic composition according to claim 17, wherein said inorganic pigment is selected from the group consisting of an iron oxide, titanium dioxide, zinc oxide, potassium ferricyanide ($K_3Fe(CN)_6$), potassium ferrocyanide ($K_4Fe(CN)_6$, potassium ferrocyanide trihydrate ($K_4Fe(CN)_6 3H_2O$, and mixtures thereof, and wherein said inorganic filler is selected from the group consisting of mica, talc, silica, and mixtures thereof.*

*19. A method of reducing staining potential of a lip product on a person, comprising applying to the person a water and oil repellent lip product comprising:*

*a plurality of particulates selected from inorganic pigments, inorganic fillers, and lakes, said particulates having a coating consisting of a fluorosilane having the formula $CF_3CF_2CF_2CF_2CF_2CF_2CH_2CH_2Si(OCH_2CH_3)_3$;*

*a vehicle suitable for application to the lips; and*

*an ingredient selected from the group consisting of: a chelating agent, a film former, a plasticizer, a resin, a retinoid, a skin penetration enhancer, a stabilizer, a sunscreen, a vitamin, a wax, and any combinations thereof;*

*wherein said fluorosilane is about 0.0015 wt % to about 0.30 wt % of the total weight of the lip product.*

*20. A method of improving water and/or oil resistance in a mascara on a person, comprising applying to a person a water and oil repellant mascara comprising:*

*a plurality of particulates selected from inorganic pigments, inorganic fillers, and lakes, said particulates having a coating consisting of a fluorosilane having the formula $CF_3CF_2CF_2CF_2CF_2CF_2CH_2CH_2Si(OCH_2CH_3)_3$;*

*a vehicle suitable for application to the eyelashes; and*

*an ingredient selected from the group consisting of: a chelating agent, a film former, a plasticizer, a resin, a retinoid, a skin penetration enhancer, a stabilizer, a sunscreen, a vitamin, a wax, and any combinations thereof;*

*wherein said fluorosilane is about 0.01 wt % to about 0.5 wt % of the total weight of the mascara.*

*21. A method of improving wear resistance of a cosmetic having a plurality of particulates comprising applying to a person a water and oil repellant cosmetic composition comprising:*

*a plurality of particulates selected from inorganic pigments, inorganic fillers, and lakes, said particulates having a coating consisting of a fluorosilane having the formula $CF_3CF_2CF_2CF_2CF_2CF_2CH_2CH_2Si(OCH_2CH_3)_3$;*

*a vehicle suitable for application to the skin; and*

*an ingredient selected from the group consisting of: a chelating agent, a film former, a plasticizer, a resin, a retinoid, a skin penetration enhancer, a stabilizer, a sunscreen, a vitamin, a wax, and any combinations thereof;*

*wherein said cosmetic composition is a product selected from the group consisting of a an eye shadow, and wherein said fluorosilane is about 0.01 wt % to about 1.5 wt % of the total weight of the cosmetic composition;*

*a liquid make-up, and wherein said fluorosilane is about 0.01 wt % to about 0.5 wt % of the total weight of the cosmetic composition;*

*a concealer; and*

*a cream make-up.*

22. A method of reducing oil breakthrough in a facial product on a person, comprising applying to the person a water and oil repellant facial product comprising:

a plurality of particulates selected from inorganic pigments, inorganic fillers, and lakes, said particulates having a coating consisting of a fluorosilane having the formula $CF_3CF_2CF_2CF_2CF_2CF_2CH_2CH_2Si(OCH_2CH_3)_3$;

a vehicle suitable for application to the face; and an ingredient selected from the group consisting of: a chelating agent, a film former, a plasticizer, a resin, a retinoid, a skin penetration enhancer, a stabilizer, a sunscreen, a vitamin, a wax, and any combinations thereof.

23. A method of reducing color drift in a powder cosmetic during wear on a person, comprising applying to the person a water and oil repellant powder cosmetic comprising:

a plurality of particulates selected from inorganic pigments, inorganic fillers, and lakes, said particulates having a coating consisting of a fluorosilane having the formula $CF_3CF_2CF_2CF_2CF_2CF_2CH_2CH_2Si(OCH_2CH_3)_3$;

a vehicles suitable for application to skin; and an ingredient selected from the group consisting of: a cheating agent, a film former, a plasticizer, a resin, a retinoid, a skin penetration enhancer, a stabilizer, a sunscreen, a vitamin, a wax, and any combinations thereof;

wherein said powder cosmetic is a powder, a blush or an eye shadow, and wherein said fluorosilane is about 0.01 wt % to 1.5 wt % of the total weight of the powder cosmetic.

24. The cosmetic composition according to claim 15, wherein said fluorosilane comprises about 0.01 wt % to about 2.0 wt % of the total weight of the coated particulates.

* * * * *